(12) United States Patent
Zonneveld et al.

(10) Patent No.: US 6,256,528 B1
(45) Date of Patent: Jul. 3, 2001

(54) X-RAY SCANNER WITH MEANS FOR CONVENTIONAL RADIOGRAPHY

(75) Inventors: Frans W. Zonneveld; Johannes C. A. Op De Beek, both of Eindhoven (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/018,981

(22) Filed: Feb. 5, 1998

(30) Foreign Application Priority Data

Feb. 14, 1997 (EP) .................................................. 97200417
Jun. 6, 1997 (EP) .................................................. 97201724

(51) Int. Cl.$^7$ ...................................................... A61B 5/00
(52) U.S. Cl. .............................. 600/425; 5/601; 378/167; 378/173; 378/177; 378/181; 378/209
(58) Field of Search ................................ 600/425; 5/601; 378/4, 20, 21, 28, 62, 63, 167, 177, 181, 208, 209, 171, 173

(56) References Cited

U.S. PATENT DOCUMENTS

| | | | |
|---|---|---|---|
| 4,942,597 | 7/1990 | Van Acker et al. | 378/197 |
| 5,132,541 | 7/1992 | Conrads et al. | 250/370.01 |
| 5,185,777 | 2/1993 | Hasegawa | 378/176 |
| 5,276,329 | 1/1994 | Hughes | 250/370.11 |
| 5,365,565 | 11/1994 | Barbaric | 378/146 |
| 5,490,508 | * 2/1996 | Kato | 600/422 |
| 5,751,781 | * 5/1998 | Brown et al. | 378/65 |

FOREIGN PATENT DOCUMENTS

| | | |
|---|---|---|
| 4210423C1 | 4/1993 | (DE) . |
| 647040A | 2/1994 | (JP) . |

* cited by examiner

*Primary Examiner*—Ruth S. Smith
(74) *Attorney, Agent, or Firm*—John F. Vodopia

(57) ABSTRACT

The scanner includes a patient table having a table support and a moveable table top for receiving a patient. The scanner further includes a computer tomography (CT) imaging device for obtaining an image of a patient placed on the table top. The CT imaging device has an X-ray source and an X-ray detector mounted for rotation about an axis substantially parallel to the longitudinal direction of the table top, the table top being movable along this axis. Also included are a second conventional radiographic imaging device having a cassette for receiving a sheet of an x-ray sensitive material. The table top has a chamber for receiving the cassette of a length that is substantially equal to the length of the table top. Preferably, this chamber contains a trolley for carrying the cassette and a driving device for moving the trolley in the longitudinal direction of the table top over substantially the full length of the chamber.

10 Claims, 5 Drawing Sheets

X-RAY SCANNER WITH MEANS FOR CONVENTIONAL RADIOGRAPHY

BACKGROUND OF THE INVENTION

1. Field of the Invention

The invention relates to an X-ray scanner including a patient table having a table top for receiving a patient, first imaging means for obtaining an image of a patient placed on the table top by of computed tomography, the first imaging means comprising an X-ray source and an X-ray detector, which are driven together by a rotational driving mechanism and are mounted so as to be rotatable about an axis of rotation which is substantially parallel to the longitudinal direction of the table top and extends through an examination space, and second imaging means for obtaining an image of the patient on the table top by radiography, the second imaging means including detection means sensitive to X-rays.

2. Description of Related Art

An X-ray scanner of this type is known from the English-language abstract of JP-A-6-47040. The known device comprises a table top that is slidable on a table support. The table top comprises a first portion for cooperation with the first imaging means and a second portion for cooperation with the second imaging means. The second imaging means comprise a second X-ray source located at some distance from the first imaging means and a cassette for receiving a material that is sensitive to X-rays that is located in the table support, opposite the second X-ray source. In order to obtain images of a given part of a patient by means of CT and by means of conventional radiography, the patient has to be moved in the longitudinal direction of the table top so that the said part is first located on the first portion of the table top and then on the second portion. This moving is inconvenient and sometimes even dangerous, e.g. for patients in trauma. Moreover, the table top must be very long in order to enable the movement of the patient over a distance sufficient to image each part of the patient by means of CT and radiography.

SUMMARY OF THE INVENTION

It is an object of the invention to provide an X-ray scanner of the kind set forth in which it is possible to obtain images by means of CT and conventional radiography without moving the patient relative to the table top. The X-ray scanner according to the invention is characterized in that the table top comprises a chamber for receiving the detection means, said chamber having a length that is substantially equal to the length of the table top.

It should be noted that the detection means can be designed in several forms which are well known per se. The detection means may be implemented as a digital detector having as many X-ray sensitive detection elements as there are image pixels to be stored. Such a digital detector is known, for example from the U.S. Pat. Nos. 5,132,541 or 5,276,329. The detection means may also be implemented as a conventional cassette for receiving a sheet that is sensitive to X-rays. Wherever the term "cassette" is used hereinafter, it should be understood to mean also a digital detector as indicated above.

For conventional radiography, the cassette or the digital detector can be placed inside the chamber at the location of the portion of the patient that has to be imaged and for CT the cassette or the digital detector can be removed from this location so that the table top is transparent to X-rays again as required for the proper operation of the first imaging means. As a result, it is only the cassette or the digital detector and not the patient that has to be moved.

It is possible to slide the cassette or the digital detector into and out of the chamber by hand. However, operation of the X-ray scanner is more convenient in an embodiment that is characterized in that the chamber contains a trolley for carrying the detection means, driving means being provided for moving said trolley in the longitudinal direction of the table top over substantially the full length of the chamber.

The driving means may comprise any known device, for example a belt drive as disclosed in DE-C-42 10 423, but a preferred embodiment is characterized in that the driving means comprise a telescopic tube extending parallel to the longitudinal direction of the table top and hydraulic means for varying the length of the telescopic tube. Such a device is simple to operate and it occupies very little space when the telescopic tube has its shortest length, i.e. when the trolley is at a position near the end of the table top where the cassette or the digital detector can be removed from the table top.

For some examinations it is sufficient to obtain a single image by means of conventional radiography. However, for other examinations it may be desirable to make a series of images. In that case, when using a cassette for receiving a sheet comprising a material that is sensitive to X-rays as a detection means, the cassette can be moved to the end of the table top after each exposure so as to replace the exposed sheet (which is e.g. a photographic film or a selenium plate) by a fresh one. This is rather inefficient and a much simpler procedure is made possible by a further embodiment of the device in accordance with the invention, which is characterized in that # the cassette comprises a sheet dispenser and a sheet holder, the sheet dispenser comprising at least a first compartment for receiving unexposed sheets and a second compartment for receiving exposed sheets, the cassette further comprising transport means for transporting unexposed sheets from the first compartment to the sheet holder and for transporting exposed sheets from the sheet holder to the second compartment. In this embodiment the sheets can be exchanged while the cassette remains in the position for making radiographic images.

In some cases it may be desirable to obtain radiographic images of the whole body (or a substantial portion of the body) of a patient. An embodiment which makes this possible is characterized in that the detection means has a length that is substantially equal to the length of the chamber, the X-ray source being shared by the first imaging means and the second imaging means. This embodiment has the further advantage that a second X-ray source for radiography can be dispensed with so that the device is less expensive and smaller.

These and other aspects of the invention will be explained in detail with reference to the drawing.

DETAILED DESCRIPTION OF THE PREFERRED EMBODIMENT

Figure 1:
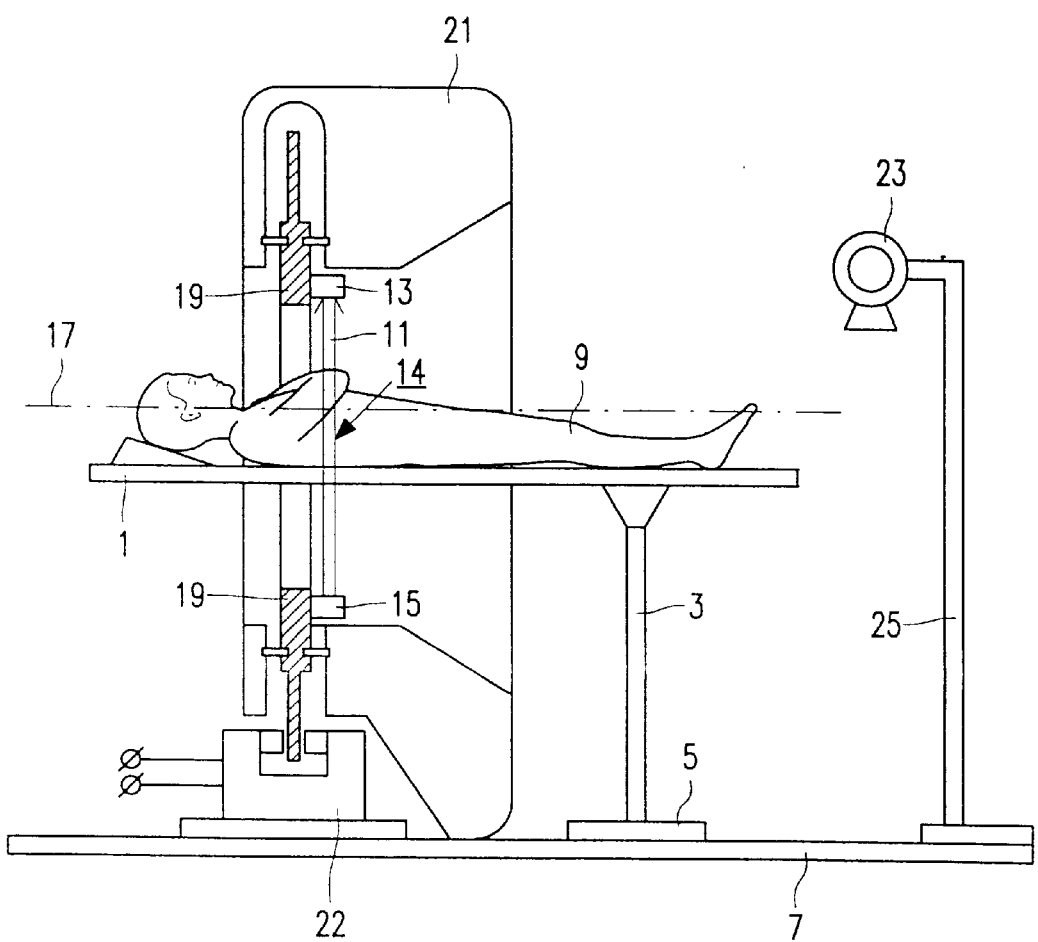
FIG. 1 is a schematic representation of the general lay-out of an embodiment of an X-ray scanner in accordance with the invention.

The X-ray scanner shown in FIG. 1 comprises a patient table including a table top 1 which is mounted on a table support 3. In this embodiment the table support 3 is mounted on a carriage 5 which can be translated with respect to a base plate 7. It is also possible to fix the table support 3 to the base plate 7 (or the floor), the table top 1 then being movable relative to the table support. Such constructions are well known in the art. It is also well known in the art to give the table top the possibility of a rotation about an axis that is perpendicular to the table top or a rotation about an horizontal axis that is perpendicular to the latter axis as well as to the longitudinal direction. The first mentioned rotation is called swivel, the latter one is called tilt. Using the swivel movement the carriage 5 can translate with respect to the base plate in a sidelong direction (i.e. transverse to the plane of the drawing); using the tilt movement the table top 1 rotates with respect to table support 3, the height of support 3 being automatically adapted to keep the part of the table top in the area of interest in the same position. The table top 1 is a substantially rectangular structure that has sufficient length for a patient 9 to lie on it, e.g. 2 m. The patient 9 can be irradiated by a flat fan-shaped X-ray beam 11 emitted by an X-ray source 13 and passing an examination space 14. Radiation transmitted by the patient is measured by means of an X-ray detector 15 which comprises a series of detector elements arranged along the arc of a circle. The X-ray source 13 and the detector 5 can be rotated together about an axis of rotation 17 directed transverse to the X-ray beam 11 and parallel to the longitudinal direction of the table top 1. By means of a computer (not shown) the density distribution of the patient 9 in a cross-section irradiated by the flat beam 11 can be calculated from the detector signals. An accurate calculation can be carried out when the X-ray source 13 with the detector 15 is rotated through an angle of at least 360°; however, a rotation over an angle of 180° plus the divergence angle of the x-ray beam is sufficient for the reconstruction of the image. For this purpose, the X-ray source 13 and the detector 15 are mounted on a ring 19 which is rotatably arranged in a gantry 21. It should be noted that the envelope constituted by the gantry 21 envelopes all movable parts connected to ring 19 so as to prevent collision of the patient with the moving parts. A motor 22 is provided to rotate the ring 19 about the axis of rotation 17. The motor 22 and the ring 19 are part of a rotational driving mechanism that is described in more detail e.g. in U.S. Pat. No. 4,942,597. The X-ray source 13, the detector 15 and the driving mechanism are parts of first imaging means for obtaining an image of a cross-section of (a part of) the patient 9 by means of computer tomography (CT).

The X-ray scanner shown in FIG. 1 further comprises second imaging means for obtaining an image of the patient 9 by conventional radiography. The second imaging means comprise a further X-ray source 23 which may be mounted on a support 25 that rests on the base plate 7. Alternatively, the further X-ray source 23 may be suspended from the ceiling. The second imaging means further comprise a cassette (not shown in FIG. 1) for receiving one or more sheets comprising a material that is sensitive to X-rays. Such sheets may be e.g. photographic film or selenium plates. According to the invention, the cassette is located in a chamber that is recessed in the interior of the table top 1.

Figure 2:
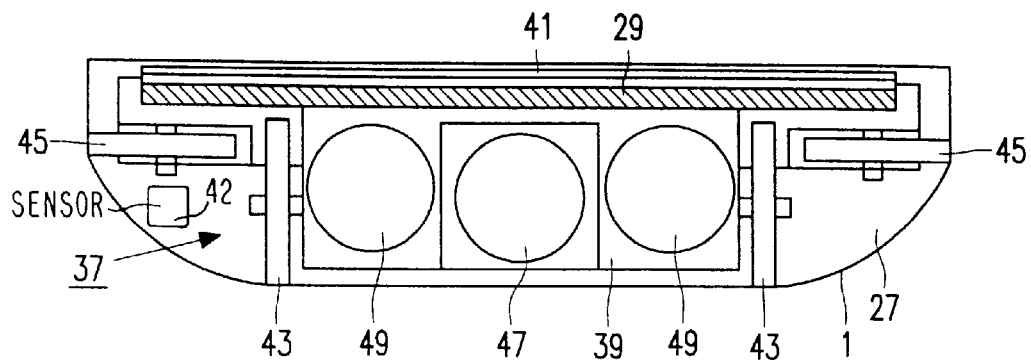
FIG. 2 shows a cross-section of a first embodiment of a table top for the apparatus shown in FIG. 1 with a trolley and a cassette.
Figure 3:
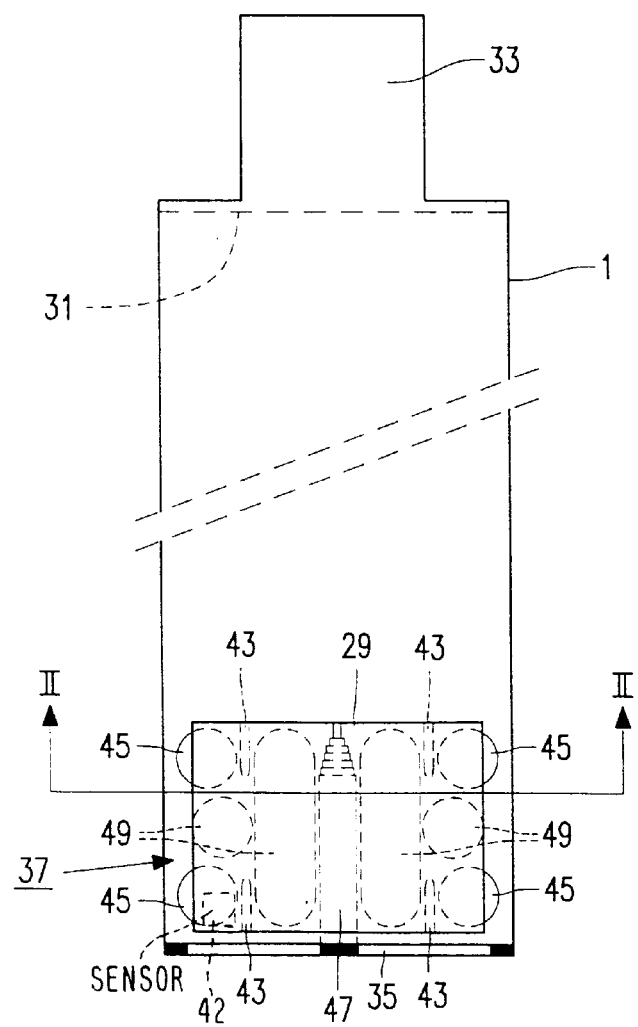
FIG. 3 shows a view from above of the table top shown in FIG. 2 with the trolley in a first position.
Figure 4:
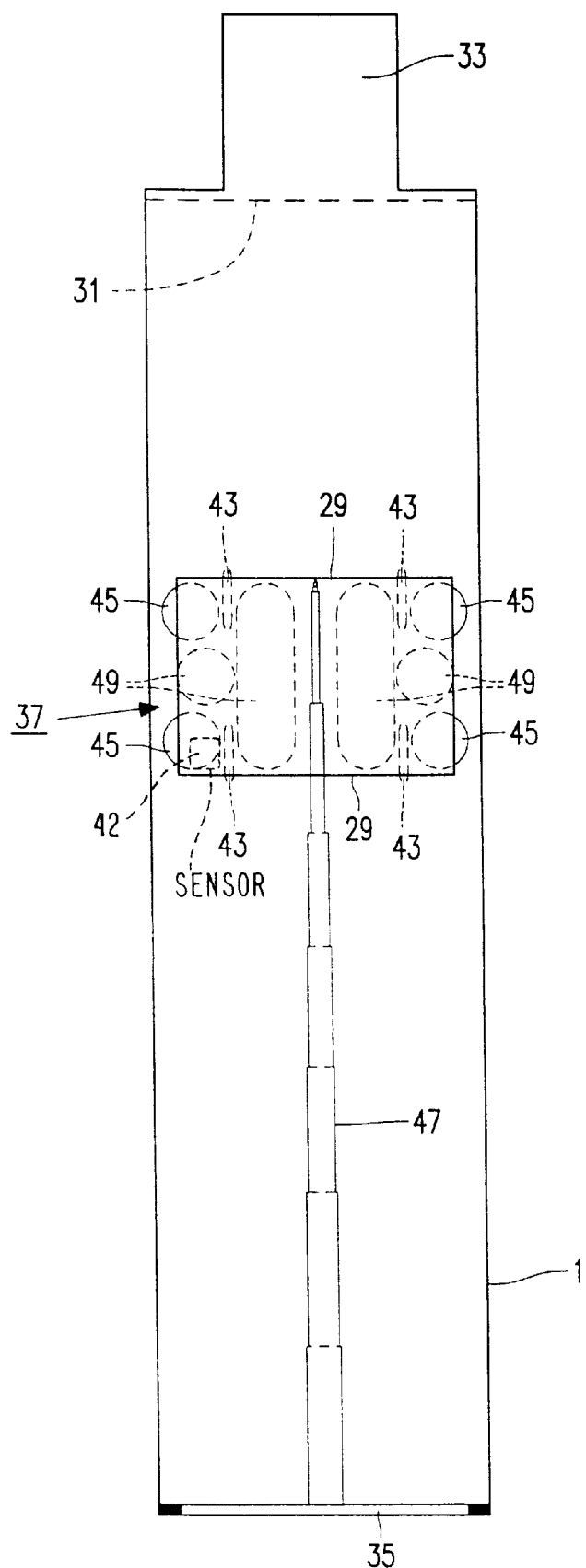
FIG. 4 shows a view similar to FIG. 3 with the trolley in a second position.

FIGS. 2, 3 and 4 illustrate a first embodiment of the table top with the cassette in the chamber. FIG. 2 shows a cross-section according to the line II—II in FIG. 3 and FIGS. 3 and 4 show views from above. The table top 1 is a hollow structure with preferably a flat surface on top and a curved surface on the bottom not to interfere with the central aperture in the gantry 21. This structure has been made from a material that has sufficient mechanical strength and stiffness and is transparent to X-rays. Suitable materials are e.g. epoxy graphite or kevlar-reinforced resin. In the interior of the table top 1 a chamber 27 is recessed for receiving a cassette 29. The chamber extends from a first end of the table top 1 (on the right in FIG. 1) over substantially the whole length of the table top. In FIGS. 3 and 4 the end of the chamber 27 is indicated by a dotted line 31 which is located near the other end of the table top 1. In this embodiment, the chamber 27 ends just in front of a head-rest 33 that is a relatively narrow part at the end of the table top 1. If necessary it would, of course, be possible to give the head-rest 33 the same width as the rest of the table top 1 and to make the chamber 27 extend into the head-rest.

At its end remote from the head-rest 33 the table top 1 is provided with a lid 35 that gives access to the chamber 27 so that the cassette 29 can be inserted into and removed from the chamber. The cassette 29 could be positioned in the chamber by sliding it along the chamber by hand, e.g. by means of a tool attachable to the cassette. In the embodiment shown in FIGS. 2–4, however, a more sophisticated means of transportation is provided. This transportation means comprises a trolley 37 that carries the cassette 29. The trolley 37 comprises a frame 39 on which the cassette 29 can be loaded when the trolley is at the end of the table top I that is remote from the head-rest 33. The frame 39 may additionally have provisions for accommodating a vibrating grid 41 as is frequently used in radiography. The frame 39 is provided with translation wheels 43 on the bottom for translation of the trolley 37 in the longitudinal direction of the chamber 27 and with guiding wheels 45 on the side for keeping the trolley in the center of the chamber.

Transportation means are provided for moving the trolley 37 over the full length of the chamber 27. Such transportation means could include an electric motor mounted on the trolley or a couple of driving belts along the long sides of the chamber 27 as disclosed in DE-C-42 10 423. A motor has the disadvantage that it should not be located underneath the cassette 29 because it takes away too much room that could be used for the cassette. Therefore, the motor should be located at one end of the frame 39 where it is not in the path of the X-rays from the further X-ray source 23 to the cassette 29 or in the path of the X-rays from the X-ray source 13 to the cassette 29. Consequently, the length of the trolley would have to be increased. Driving belts have the disadvantage that they are always in the chamber so that they are also in the path of the beam 11 of the first imaging means shown in FIG. 1. These disadvantages are avoided by the driving means of the embodiment shown in FIGS. 2–4. These driving means include a telescopic tube 47 that extends through the chamber 27 parallel to the longitudinal direction of the table top 1. The length of the tube 47 can be varied hydraulically by pumping oil into the tube. Constructions of this type are well known in the art, e.g. for lifting the loading platform of a truck. The oil required for this purpose can be stored in containers 49 provided on the trolley 37.

Of course, the trolley 37 with the cassette 29 should be positioned accurately underneath the further X-ray source 23 shown in FIG. 1. This can be done manually by entering the position or it can be done automatically or semi-automatically. A semi-automatic method is by pointing a magnetic device to the required position of the cassette 29 at the outside of the table top 1. A sensor 42 on the trolley 37 picks up the signal from this device and with the aid of the sensor signal the trolley is guided to the required location. When the further X-ray source 23 is ceiling-mounted, and when it is positioned directly above the patient 9, it may automatically signal its position to the trolley 37 which then follows the X-ray source to the right location. Such positioning means are well known in the art and will not be described in detail here. It is also possible to measure the amount of oil that has been pumped into the tube 47 for establishing the position of the trolley. This amount constitutes a direct measure for that position which can be established by means of f.i. a look-up table that gives the relation between the amount of oil and the position of the trolley. After the radiograph has been taken, the trolley 37 can be brought to the end of the table top 1 remote from the head-rest 33 and the cassette 29 can be unloaded via the lid 35.

The first embodiment described above is very suitable for making a single radiographic image of the patient 9. In some cases, however, it is necessary to obtain a plurality of radiographic images, e.g. for a quick radiological survey of a polytraumatic patient. In such cases it is inconvenient that after each radiograph the cassette 29 must be returned to the end of the table top 1 to be exchanged for a new one with an unexposed film. Therefore, a second and a third embodiment of the X-ray scanner have been developed, which are especially adapted to the making of a radiological survey of a whole patient or a large part of a patient in a relatively short time.

Figure 5:
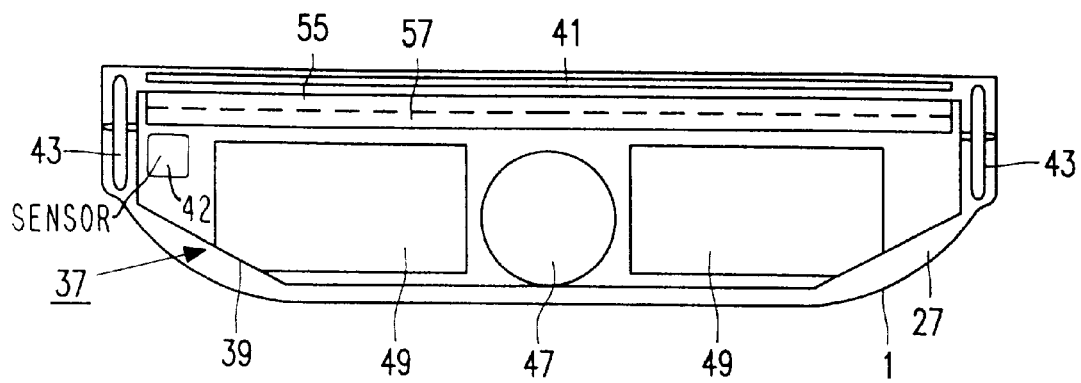
FIG. 5 shows a cross-section of a second embodiment of a table top for the apparatus shown in FIG. 1 with a trolley and a cassette comprising a sheet dispenser and a sheet holder.
Figure 6:
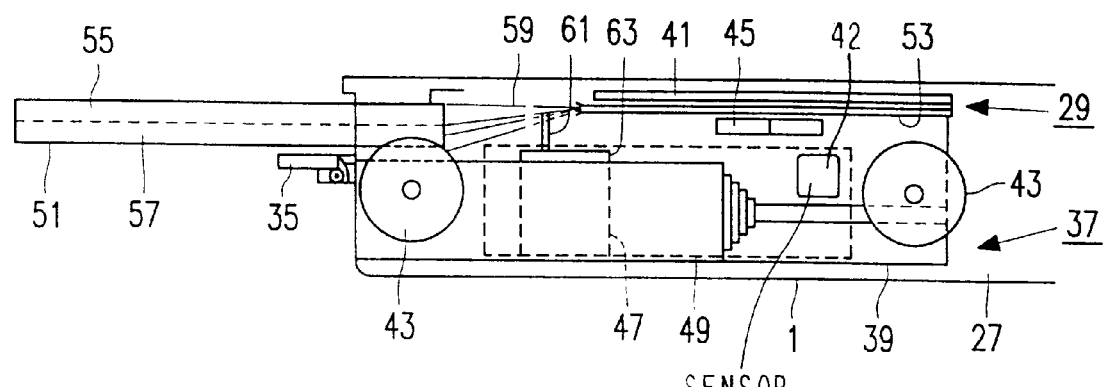
FIG. 6 shows a longitudinal section of a part of the table top shown in FIG. 5.

FIG. 5 shows a cross-section similar to FIG. 2 of the second embodiment and FIG. 6 shows a longitudinal section of the end portion remote from the head-rest 33 of the table top 1 of the second embodiment. For those parts that correspond to parts of the first embodiment, the same reference numerals have been used as in FIGS. 2–4. The trolley 37 and the driving means 47,49 of the second embodiment have substantially the same construction as in the first embodiment but in the second embodiment the trolley 37 is somewhat longer to accommodate the cassette 29 which is also longer than the cassette of the first embodiment. The cassette 27 of the second embodiment comprises a sheet dispenser 51 and a sheet holder 53. The sheet dispenser 51 comprises a first compartment 55 for receiving unexposed sheets (e.g. X-ray sensitive film or selenium plates) and a second compartment 57 for receiving exposed sheets. The sheet holder is conceived to hold a sheet in place during the exposure. Transport means are provided for transporting unexposed sheets from the first compartment 55 to the sheet holder 53 and for transporting exposed sheets from the sheet holder to the second compartment 57. The transport means comprise a sheet guide 59 which is pivotable so that it can establish a first path for sheets between the first compartment 55 and the sheet holder 53 and a second path between the sheet holder and the second compartment 57. The position of the sheet guide 59 may be controlled by an actuator 61, e.g. a piezoelectric or a pneumatic actuator which is energized by a control unit 63 that also provides energy for transporting the sheets. The transportation of the sheets may be achieved e.g. by a vacuum system or a system using pressurized air. Such transport systems are well known in the art. When the trolley 37 is moved to the end of the table top 1, the sheet dispenser 51 pushes the lid 35 open so that the sheet dispenser extends partly outside the chamber as shown in FIG. 6. It is then easy to remove the sheet dispenser 51 and to replace it with a new one loaded with unexposed sheets.

Figure 7:
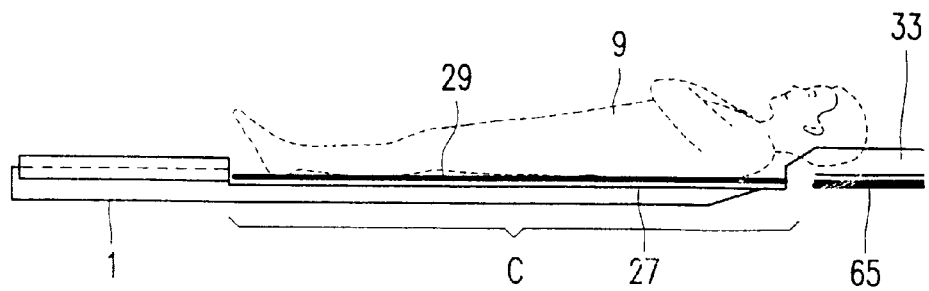
FIG. 7 shows a side elevation of a third embodiment of a table top for the apparatus shown in FIG. 1.
Figure 8:
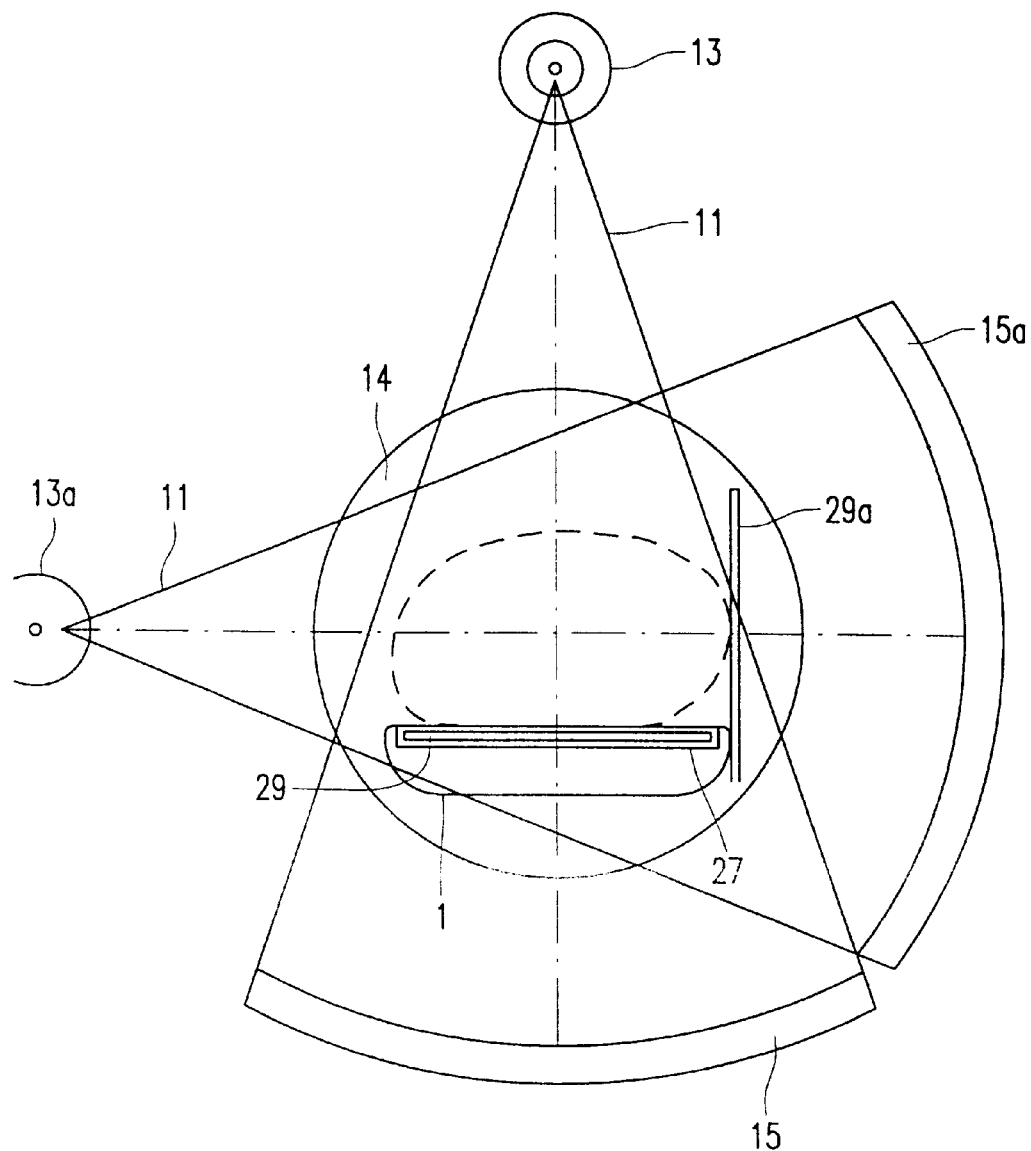
FIG. 8 is an illustration of the operation of the apparatus including the embodiment of the table top shown in FIG. 7.

FIG. 7 shows a side elevation of the third embodiment and FIG. 8 illustrates the operation of this embodiment. Components that correspond to components shown in the previous Figures have been indicated with the same reference numerals. In the third embodiment, the cassette 29 has a length that is substantially equal to the length c of the chamber 27 recessed in the table top 1 so that it substantially completely fills the chamber. A small separate cassette 65 for imaging the head of the patient 9 may be provided under the head-rest 33. Although a transport means for transporting the cassette 29 (such as the trolley 37) could be provided, it is in this embodiment preferable to slide the cassette into and out of the chamber 27 so that no extra space for a trolley is required. In this embodiment, the X-ray source 13 of the first imaging means is preferably used as a part of the second imaging means as well. This has the advantage that the scanner is simpler and less expensive than in the first and second embodiments where an additional X-ray source 23 is used in the second imaging means. A further advantage is that the X-ray source 13 of the first imaging means usually comprises an X-ray tube that is highly powered and capable of a patient-long scanogram. To make such a scanogram, the table top 1 with the patient 9 on it is moved in its longitudinal direction so that the whole patient passes the examination space 14. During this movement of the table top, the ring 19 is held stationary in such a position that the line connecting the centers of the X-ray source 13 and the detector 15 is vertical. This is the position shown in FIG. 8. With the X-ray source 13 and the detector IS in this position, an image of the patient 9 in the AP direction can be obtained. The torso and the extremities of the patient 9 can be imaged together on one film or, alternatively, on a plurality of smaller films located adjacently in the cassette 29. For obtaining a lateral view of the patient, the ring 19 can be rotated over 90° so that the X-ray source and the detector are positioned on a horizontal line. In FIG. 8 these positions of the X-ray source and the detector are indicated as 13a and 15a, respectively. The cassette must then also be rotated over 90° as indicated at 29a. This can be the same cassette that is used inside the chamber 27 or another cassette with extra provisions to clamp it to the side of the table top 1.

The detector 15 can be used to measure the amount of radiation passing through the patient 9 and the information produced by the detector can be used to adjust the dose to a desired value.

All references cited herein, as well as the priority documents European Patent Applications 97200417.0 filed Feb. 14, 1997 and 97201724.8 filed Jun. 6, 1997, are incorporated herein by reference in their entirety and for all purposes to the same extent as if each individual publication or patent or patent application was specifically and individually indicated to be incorporated by reference in its entirety for all purposes.

What is claimed is:
1. An X-ray scanner comprising:
   a patient table comprising a table support and a table top for receiving a patient, said table top being elongated in a longitudinal direction, first X-ray imaging means for obtaining an image of a patient placed on the table top by means of computed tomography (CT), said first imaging means comprising a first X-ray source and an X-ray detector, which are driven together by a rotational driving mechanism and are mounted so as to be rotatable about an axis of rotation which is substantially parallel to the longitudinal direction of the table top and extends through an examination space, at least the table top being movable in its longitudinal direction relative to the examination space, and second X-ray imaging means for obtaining an image of the patient placed on the table top by means of radiography, said second imaging means comprising a second X-ray source and detection means sensitive to X-rays, wherein the table top comprises a chamber for receiving the detection means, said chamber having a length in the longitudinal direction that is substantially equal to the length of the table top in the longitudinal direction, wherein the first and the second X-ray sources are differently positioned, wherein the table top is further movable so that the first and the second X-ray imaging means can obtain images of the same selected portions of the patient without patient motion relative to the table top, and wherein the detection means is moveable within the chamber (i) relative to the first X-ray source in order that an image can be obtained by the first imaging means without interference by the detection means, and (ii) relative to the second X-ray source in order to detect an image obtained by the second imaging means.

2. An X-ray scanner as claimed in claim 1, in which the chamber contains a trolley for carrying the detection means, driving means being provided for moving said trolley in the longitudinal direction of the table top over substantially the full length of the chamber, wherein movement of the trolley is relative to the first and to the second X-ray sources in order to obtain images by both the first and the second imaging means.

3. An X-ray scanner as claimed in claim 2, in which the driving means comprise a telescopic tube extending parallel to the longitudinal direction of the table top and hydraulic means for varying the length of the telescopic tube.

4. An X-ray scanner as claimed in claim 3, in which the detection means are constituted by a cassette for receiving a sheet comprising a material that is sensitive to X-rays, which cassette comprises a sheet dispenser and a sheet holder, the sheet dispenser comprising at least a first compartment for receiving unexposed sheets and a second compartment for receiving exposed sheets, the cassette further comprising transport means for transporting unexposed sheets from the first compartment to the sheet holder and for transporting exposed sheets from the sheet holder to the second compartment.

5. An X-ray scanner as claimed in claim 2, in which the detection means are constituted by a cassette for receiving a sheet comprising a material that is sensitive to X-rays, which cassette comprises a sheet dispenser and a sheet holder, the sheet dispenser comprising at least a first compartment for receiving unexposed sheets and a second compartment for receiving exposed sheets, the cassette further comprising transport means for transporting unexposed sheets from the first compartment to the sheet holder and for transporting exposed sheets from the sheet holder to the second compartment.

6. A moveable patient table for use in a x-ray scanner having a first X-ray imaging means including a CT scanner and a second X-ray imaging means including a conventional radiograph, the two x-ray image means having a first and a second differently positioned X-ray source, the table comprising:

a table support and a table top for receiving a patient, said table top being elongated in a longitudinal direction, wherein the table top comprises a chamber within which is disposed a detection means sensitive to X-rays, said chamber having a length in the longitudinal direction that is substantially equal to the length of the table top in the longitudinal direction, wherein the table top is further movable so that the first and second X-ray imaging means can obtain images of the same selected portions of the patient without patient motion relative to the table top, and wherein the detection means within the chamber is at least partially automatically moveable within the chamber (i) relative to the first X-ray source in order that an image can be obtained by the first imaging means without interference by the detection means, and (ii) relative to the second X-ray source in order to detect an image obtained by the second imaging means.

7. A patient table as claimed in claim 6, in which the chamber contains a trolley for carrying the detection means, driving means being provided for moving said trolley in the longitudinal direction of the table top over substantially the full length of the chamber, wherein movement of the trolley is relative to the first and to the second X-ray sources in order to obtain images by both the first and the second imaging means.

8. A patient table as claimed in claim 7, in which the driving means comprise a telescopic tube extending parallel to the longitudinal direction of the table top and hydraulic means for varying the length of the telescopic tube.

9. The patient table of claim 7, wherein the trolley further comprises a sensor for picking up a positioning signal and a means for providing the positional signal which indicates a required position of the detection means relative to the second X-ray source in order to obtain an image by the second imaging means.

10. A patient table as claimed in claim 6 in which the detection means has a length which is substantially equal to the length of the chamber.

* * * * *